(12) United States Patent
Quan et al.

(10) Patent No.: US 9,579,515 B2
(45) Date of Patent: *Feb. 28, 2017

(54) DETERMINATION FOR EFFECTIVE DEFIBRILLATION

(71) Applicant: ZOLL Medical Corporation, Chelmsford, MA (US)

(72) Inventors: Weilun Quan, Dracut, MA (US); Qing Tan, Somerville, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,060

(22) Filed: Oct. 8, 2015

(65) Prior Publication Data

US 2016/0023010 A1   Jan. 28, 2016

Related U.S. Application Data

(63) Continuation of application No. 14/483,377, filed on Sep. 11, 2014, now Pat. No. 9,180,304, which is a
(Continued)

(51) Int. Cl.
*A61N 1/39* (2006.01)

(52) U.S. Cl.
CPC ......... *A61N 1/3925* (2013.01); *A61N 1/3937* (2013.01); *A61N 1/3993* (2013.01); *A61N 1/3987* (2013.01)

(58) Field of Classification Search
CPC .. A61N 1/3937; A61N 1/3987; A61N 1/3925; A61N 1/3993
(Continued)

(56) References Cited

U.S. PATENT DOCUMENTS 5,077,667 A    12/1991    Brown et al.
5,092,341 A    3/1992    Kelen
(Continued)

FOREIGN PATENT DOCUMENTS

WO    2011/100534    8/2011
WO    2012/059846    5/2012
(Continued)

OTHER PUBLICATIONS

International Search Report and Written Opinion, PCT/US2012/64779, Feb. 1, 2013, 8 pages.
(Continued)

*Primary Examiner* — Christopher D Koharski
*Assistant Examiner* — Michael Carey
(74) *Attorney, Agent, or Firm* — Fish & Richardson P.C.

(57) ABSTRACT

A method for managing care of a person receiving emergency cardiac is disclosed and involves monitoring, with an external defibrillator, multiple parameters of the person receiving emergency cardiac assistance; determining from at least one of the parameters, an indication of trans-thoracic impedance of the person receiving emergency cardiac care; determining, from at least one of the parameters corresponding to an electrocardiogram of the person receiving emergency cardiac assistance, an initial indication of likely shock effectiveness; determining, as a function of at least the indication of trans-thoracic impedance and the initial indication of likely shock effectiveness, an indication of whether a shock provided to the person receiving emergency medical assistance will be effective; and affecting control of the defibrillator by a caregiver as a result of determining the indication of whether a shock will be effective.

16 Claims, 10 Drawing Sheets

Related U.S. Application Data continuation of application No. 13/674,602, filed on Nov. 12, 2012, now Pat. No. 8,868,179.

(60) Provisional application No. 61/558,954, filed on Nov. 11, 2011.

(58) Field of Classification Search
USPC .............................................. 607/5; 600/515
See application file for complete search history.

(56) References Cited

U.S. PATENT DOCUMENTS

| | | | |
|---|---|---|---|
| 5,741,304 A | 4/1998 | Patwardhan et al. | |
| 5,957,856 A | 9/1999 | Weil et al. | |
| 6,171,257 B1 | 1/2001 | Weil | |
| 6,224,562 B1 | 5/2001 | Lurie et al. | |
| 6,760,621 B2 | 7/2004 | Walcott | |
| 6,813,517 B2 | 11/2004 | Daynes et al. | |
| 7,269,454 B2 | 9/2007 | Sherman | |
| 7,593,772 B2 | 9/2009 | Sherman | |
| 7,774,060 B2 * | 8/2010 | Westenskow | A61M 16/00 607/5 |
| 7,813,791 B1 | 10/2010 | Gill | |
| 7,831,299 B2 | 11/2010 | Tan et al. | |
| 7,920,917 B2 | 4/2011 | Kelly | |
| 8,165,671 B2 | 4/2012 | Freeman et al. | |
| 8,868,179 B2 * | 10/2014 | Quan | A61N 1/3925 600/515 |
| 8,948,859 B2 | 2/2015 | Freeman et al. | |
| 9,180,304 B2 * | 11/2015 | Quan | A61N 1/3925 |
| 9,186,521 B2 | 11/2015 | Quan et al. | |
| 2002/0026229 A1 | 2/2002 | Weil et al. | |
| 2002/0133197 A1 | 9/2002 | Snyder et al. | |
| 2002/0138106 A1 | 9/2002 | Chiristini et al. | |
| 2003/0055460 A1 | 3/2003 | Owen et al. | |
| 2004/0039419 A1 | 2/2004 | Stickney et al. | |
| 2004/0116969 A1 | 6/2004 | Owen | |
| 2004/0215271 A1 | 10/2004 | Sullivan | |
| 2005/0080828 A1 | 4/2005 | Johnson | |
| 2005/0245974 A1 | 11/2005 | Sherman | |
| 2005/0267536 A1 | 12/2005 | Freeman et al. | |
| 2006/0025824 A1 * | 2/2006 | Freeman | A61B 5/0464 607/5 |
| 2006/0116724 A1 | 6/2006 | Snyder | |
| 2007/0060785 A1 | 3/2007 | Freeman et al. | |
| 2007/0100381 A1 | 5/2007 | Snyder et al. | |
| 2008/0145827 A1 * | 6/2008 | Strand | G09B 23/288 434/265 |
| 2008/0208070 A1 | 8/2008 | Snyder et al. | |
| 2009/0270930 A1 | 10/2009 | Walker | |
| 2010/0268059 A1 | 10/2010 | Ryu et al. | |
| 2011/0021938 A1 | 1/2011 | Anderson et al. | |
| 2011/0034816 A1 | 2/2011 | Tan et al. | |
| 2011/0202100 A1 | 8/2011 | Tan et al. | |
| 2011/0202101 A1 | 8/2011 | Tan et al. | |
| 2011/0295127 A1 | 12/2011 | Sandler et al. | |
| 2012/0010543 A1 | 1/2012 | Johnson et al. | |
| 2012/0226178 A1 | 9/2012 | Freeman et al. | |
| 2013/0138168 A1 | 5/2013 | Quan et al. | |
| 2013/0144181 A1 | 6/2013 | Fogt et al. | |
| 2013/0190634 A1 | 7/2013 | Phillips | |
| 2013/0218057 A1 | 8/2013 | Jorgenson | |
| 2014/0236030 A1 | 8/2014 | Tan et al. | |
| 2014/0277224 A1 | 9/2014 | Quan et al. | |
| 2014/0277228 A1 | 9/2014 | Quan et al. | |
| 2015/0257709 A1 | 9/2015 | Quan et al. | |
| 2015/0257715 A1 | 9/2015 | Quan et al. | |
| 2015/0352367 A1 | 12/2015 | Quan et al. | |
| 2015/0352369 A1 | 12/2015 | Quan et al. | |
| 2016/0082278 A1 | 3/2016 | Quan et al. | |

FOREIGN PATENT DOCUMENTS

| | | |
|---|---|---|
| WO | 2012/072518 | 6/2012 |
| WO | 2013/071280 | 5/2013 |

OTHER PUBLICATIONS

Extended European Search Report, PCT/US2012/065779, Aug. 14, 2015, 7 pages.
Chaudhry, Fahd A., A Novel Resuscitation Algorithm Using Waveform Analysis and End-Tidal Carbon Dioxide Pressure for Ventricular Fibrillation, University of Arizona, Biomedical Engineering Interdisciplinary Program, 2011, 39 pages.
Chinese Office Action, CN Application 201480027256.X, issued May 30, 2016, 8 pages.
Compos et al., "An Up-Down Bayesian, Defibrillation Efficacy Estimator", Pace—Pacing and Clinical Electrophysiology, Blackwell Futura Publishing, Malden, MA, US, vol. 20, No. 5, Part 01, May 1, 1997, pp. 1292-1300.
European Search Report, 14768658.8, Feb. 12, 2016, 10 pages.
Extended European Search Report, European Patent Application No. 13804051.4, dated Feb. 4, 2016, 9 pages.
Huang et al, "Quantification of activation patterns during ventricular fibrillation in open-chest porcine left ventricle and septum", Heart Rhythm Elsevier, US, vol. 2, No. 7, Jul. 1, 2005, pp. 720-728.
International Search Report and Written Opinion, PCT/US2014/027431, mailed Aug. 11, 2014, 14 pages.
International Search Report and Written Opinion, PCT/US2014/27514, mailed Aug. 11, 2014, 8 pages.
International Search Report and Written Opinion, PCT/US2014/27658, mailed Aug. 25, 2014, 19 pages.
International Search Report and Written Opinion, PCT/US2015/35174, mailed Sep. 17, 2015, 13 pages.
International Search Report and Written Opinion, PCT/US2015/35189, mailed Nov. 3, 2015, 20 pages.
International Search Report and Written Opinion from corresponding PCT/US2013/44750 mailed Sep. 20, 2013.
Lee, Seungyup, "Mapping the Characteristics of Atrial Activation Patterns During Atrial Fibrillation," Case Western Reserve University: Department of Biomedical Engineering, Jan. 2013, 34 pages.
Povoas et al., "Predicting the success of defibrillation by electrocardiographic analysis," Resuscitation 53(1):77-82 (2002).
Watson et al., "Rapid Communication; Wavelet transform-based prediction of the likelihood of successful defibrillation for patients exhibiting ventricular fibrillation; Rapid Communication", Measurement Science and Technology, IOP, Bristol, GB, vol. 16, No. 10, Oct. 1, 2005, pp. L1-L6.

* cited by examiner

DETERMINATION FOR EFFECTIVE DEFIBRILLATION

CROSS-REFERENCE TO RELATED APPLICATIONS

This application is a continuation of and claims priority under 35 U.S.C. §120 to U.S. patent application Ser. No. 14/483,377, filed Sep. 11, 2014 (which issued as U.S. Pat. No. 9,180,304), which claims benefit of priority to U.S. patent application Ser. No. 13/674,602(which issued as U.S. Pat. No. 8,868,179), filed on Nov. 12, 2012, which claims benefit of priority to U.S. Provisional Application Ser. No. 61/558,954, filed on Nov. 11, 2011, the entire contents of the above applications are hereby incorporated by reference.

TECHNICAL FIELD

This document relates to cardiac resuscitation, and in particular to systems and techniques for determining when a defibrillating shock on a person will be effective.

BACKGROUND

Heart attacks are a common cause of death. A heart attack occurs when a portion of the heart tissue loses circulation and becomes damaged as a result (e.g., because of blockage in the heart vasculature). Heart attacks and other abnormalities can lead to ventricular fibrillation, which is an abnormal heart rhythm (arrhythmia) that causes the heart to lose pumping capacity. If such a problem is not corrected quickly—typically within minutes—the rest of the body loses oxygen and the person dies. Therefore, prompt care of person undergoing ventricular fibrillation can be key to a positive outcome for such a person.

One common way to treat ventricular fibrillation is through the use of an electrical defibrillator that delivers a relatively high voltage shock to the heart in order to get it back into a normal pattern and a consistent, strong beat. People who have had previous problems may be implanted with an automatic defibrillator that constantly monitors the condition of their heart and applies a shock when necessary. Other such people may be provided with a wearable defibrillator in the form of a vest such as the LIFEVEST product from ZOLL Medical Corporation. Other people may be treated using an external defibrillator, such as in a hospital or via an automatic external defibrillator (AED) of the kind that is frequently seen in airports public gymnasiums and other public spaces.

People undergoing ventricular fibrillation may be more receptive to a defibrillating shock in some instances compared to others. For example, research has determined that a computation of amplitude spectrum area (AMSA) from an electrocardiogram (ECG) may indicate whether a shock that is delivered to a person will like cause defibrillation to occur or will instead likely fail. Naturally then, it is best to apply a shock when an AMSA value indicates that the shock will succeed, as opposed to when it indicates that the shock will fail.

SUMMARY

This document describes systems and techniques that may be used to help determine when a shock on a person suffering from VF will be successful, i.e., will defibrillate the patient. Upon making such a determination, a defibrillator may provide an indication to a rescuer about such a determination. For example, the defibrillator may only allow a shock to be performed when the indication is sufficiently positive (e.g., over a set percentage of likelihood of success). Also, a defibrillator may provide a display—such as a graphic that shows whether defibrillation will likely succeed (e.g., above a predetermine threshold level of likelihood of success) or providing a number (e.g., a percentage of likelihood of success) or other indication (e.g., a grade of A, B, C, D, or F) so that the rescuer can determine whether to apply a shock. The device can also change the indication it prevents in different situation, e.g., a dual-mode defibrillator could simply indicate whether defibrillation is advised (and may refuse to permit delivery of a shock when it is not advised) when the defibrillator is in AED mode, and may provide more nuanced information when the defibrillator is in manual mode, and thus presumably being operated by someone who can better interpret such information and act properly on it.

The determination about likelihood of success may be made as a combination of a measurement that looks to ECG values at different frequencies or frequency ranges, such as AMSA, and trans-thoracic impedance measurements of the person receiving emergency care. It has been found that patient impedance affects the AMSA threshold number at which a delivered shock will likely succeed. Thus, as discussed below, the patient trans-thoracic impedance can be used to adjust an initial AMSA measurement in order to produce a more complete indication of whether a shock will succeed on the patient. Also, the trans-thoracic impedance for the patient and the AMSA value may both be fed into a table or other form of function whose output is a separate indicator of likely success.

In certain implementations, such systems and technique may provide one or more advantages. For example, a determination of whether a shock should be provided can be made from values that are already being measured for a patient (e.g., trans-thoracic impedance may already be used by a defibrillator to affect the shape of the voltage of the waveform that is provided to the patient). The determination may be improved compared to simply measuring AMSA, and may thus result in better performance for a system and better outcomes for a patient. In particular, a defibrillator may cause a rescuer to wait to provide a defibrillating shock until a time at which the shock is more likely to be effective. As a result, the patient may avoid receiving an ineffective shock, and then having to wait another cycle for another shock (which may end up being equally ineffective). Such a process may, therefore, result in the patient returning to normal cardiac function more quickly and with less stress on his or her cardiac system, which will generally lead to better patient outcomes.

In one implementation, a method for managing care of a person receiving emergency cardiac assistance is disclosed. The method comprises monitoring, with an external defibrillator, multiple parameters of the person receiving emergency cardiac assistance; determining from at least one of the parameters, an indication of trans-thoracic impedance of the person receiving emergency cardiac care; determining, from at least one of the parameters corresponding to an electrocardiogram of the person receiving emergency cardiac assistance, an initial indication of likely shock effectiveness; determining, as a function of at least the indication of trans-thoracic impedance and the initial indication of likely shock effectiveness, an indication of whether a shock provided to the person receiving emergency medical assistance will be effective; and affecting control of the defibrillator by a caregiver as a result of determining the indication of whether a shock will be effective. The method can also include repeating cyclically the actions of monitoring, determining, and affecting control over multiple time periods during provision of emergency cardiac assistance to the person. The method can also include identifying compression depth of chest compressions performed on the person, using a device on the person's sternum and in communication with the defibrillator, and providing feedback to a rescuer performing the chest compressions regarding rate of compression, depth of compression, or both. Also, the multiple parameters can comprise signals sensed by a plurality of electrocardiogram leads.

In certain aspects, determining an initial indicator of likely shock effectiveness comprises determining a value that is a function of electrocardiogram amplitude at particular different frequencies or frequency ranges. Also, the determination of an initial indicator of likely shock effectiveness can comprise determining an amplitude spectrum area (AMSA) value. In addition, affecting control of the defibrillator can comprise preventing a user from delivering a shock unless the determination of whether a shock will be effective exceeds a determined likelihood level. Moreover, affecting control of the defibrillator can comprise electronically displaying an indicator of the determined indication of whether a shock will be effective. In other aspects, displaying an indicator comprises displaying a value, of multiple possible values in a range, that indicates a likelihood of success.

In another implementation, a system for managing care of a person receiving emergency cardiac assistance is disclosed. The system comprises one or more capacitors for delivering a defibrillating shock to a patient; one or more electronic ports for receiving signals from sensors for obtaining indications of an electrocardiogram for the patient and trans-thoracic impedance of the patient; and a patient treatment module executable on one or more computer processors to provide a determination of a likelihood of success from delivering a defibrillating shock to the person with the one or more capacitors, using both information from the electrocardiogram and from the trans-thoracic impedance.

In yet another implementation, a method for managing care of a fibrillating patient is disclosed. The method comprises generating first information indicative of an electrocardiogram of the patient; generating second information indicative of a trans-thoracic impedance of the patient; determining a likelihood of success form delivering a defibrillating shock to the patient from the first and second information; and providing to a user of a defibrillator an indication of the determination of a likelihood of success. [this is similar to claim 1 but a bit broader]

Other features and advantages will be apparent from the description and drawings, and from the claims.

DETAILED DESCRIPTION

The present disclosure is directed to systems and methods for determining whether defibrillation will be effective as a function both of an indication relating to amplitude spectrum area (AMSA) or similar measures related to analysis of electrocardiogram data, and of trans-thoracic impedance (TTI). In general, defibrillation is a common treatment for various arrhythmias, such as ventricular fibrillation (VF). However, there can be undesired side effects (e.g., heart tissue damage, skin burns, etc.) that follow an electrical shock. It is therefore desirable to predict whether defibrillation will be successful in restoring a regular heartbeat following onset of an arrhythmic episode. Such a prediction is referred to as an "indicator of success" or, equivalently, a "success indication" within the context of the present disclosure. The prediction may be used so that a defibrillating shock is not provided when the chance of successful defibrillation is low, and instead waits until the chance increases to an acceptable level. Such a determination can be used to alter care in an automatic and/or manual manner. In an automatic manner, a defibrillator may be made incapable of delivering a shock unless a success indication is above a determined amount. In a manual manner, the success indication may be shown to a rescuer, and the rescuer may determine whether to apply a shock or not based on the indication. A system may also integrate both—e.g., locking out the ability to provide a shock until a threshold level is reached, and then showing the relative likelihood of success above that value. The likelihood of success can be shown in various manners, such as by showing an actual percentage, or show two or more of a low, medium, or high likelihood of success, e.g., on a display of a defibrillator.

Figure 1:
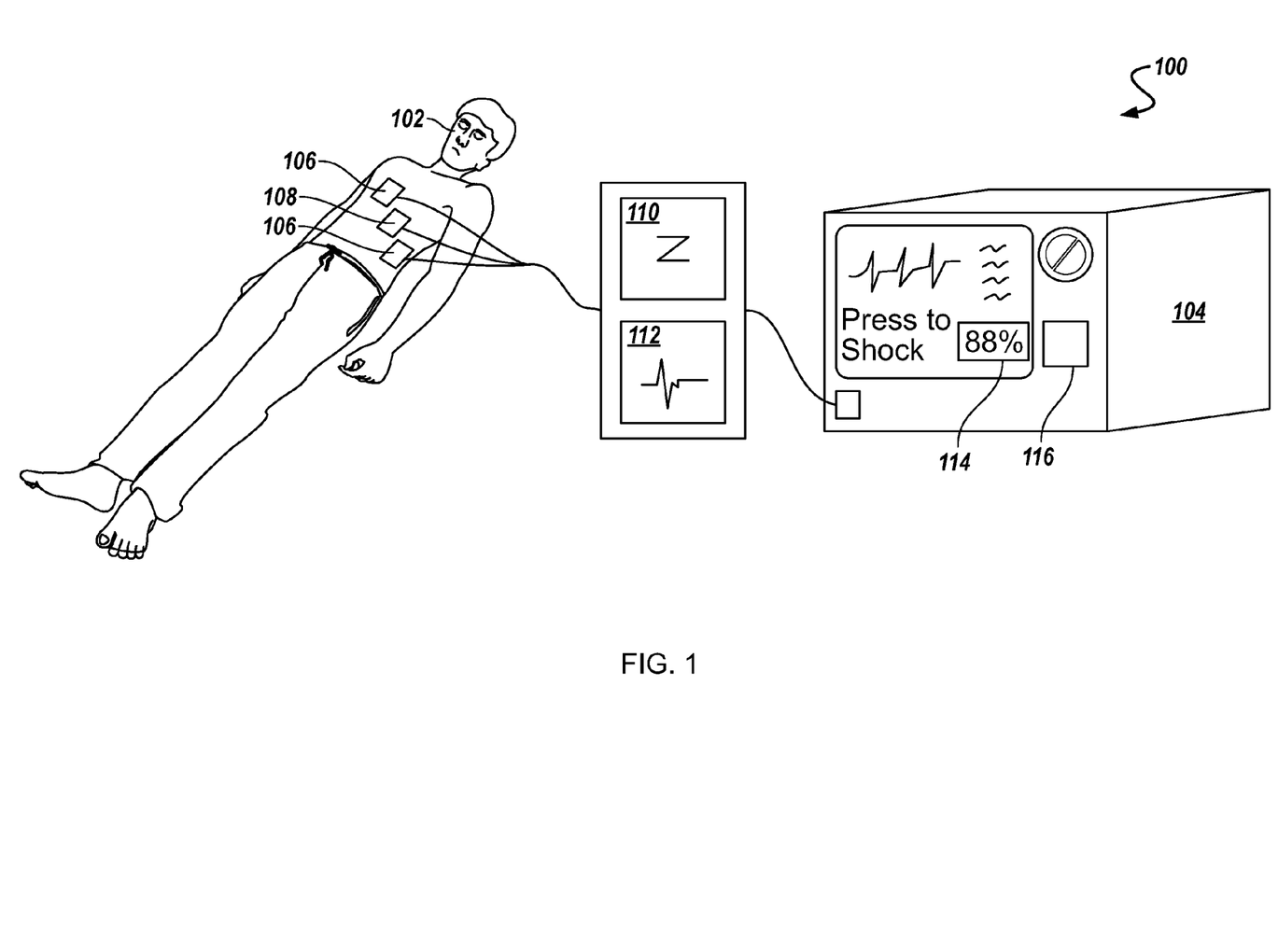
FIG. 1 shows a victim of cardiac arrest being cared for by a rescuer.

FIG. 1 shows a victim 102 of cardiac arrest being cared for by a rescuer and defibrillator 104. The defibrillator 104 includes an electrode package 106 and a compression puck 108 generally coupled thereto. An example of such a defibrillator includes the AED PLUS automated external defibrillator or the AED PRO automated external defibrillator, both from ZOLL Medical Corporation of Chelmsford, Mass. Other embodiments of the defibrillator 104 are possible.

In the pictured example, the victim 102 is rendered prone due to an arrhythmic episode, and the electrode package 106 and the compression puck 108 are positioned on the torso of the victim 102 in an appropriate and known arrangement. In accordance with the present disclosure, the defibrillator 104, in tandem with one or both of the electrode package 106 and the compression puck 108, is configured to determine whether a defibrillation shock will be an effective measure to terminate the arrhythmic episode. The determination is generally based on one or more TTI measurements and one or more calculated AMSA values.

For example, the defibrillator 104 is configured to acquire and manipulate both a TTI signal 110 and an ECG signal 112 via the electrode package 106. As described in further detail below, a TTI measurement ($\Omega$) is a parameter derived from the TTI signal 110 that represents, among other things, thoracic fluid content. An AMSA value (V-Hz) is a parameter calculated by integrating the Fourier transform of the ECG signal 112 over a finite frequency range. The AMSA value is one form of calculation that represents a value of an ECG signal from a victim, while other values may likewise be computed.

The defibrillator 104 is further configured to display an IOS indicator 114 based on the TTI measurement(s) and AMSA value(s) obtained from the TTI signal 110 and an ECG signal 112, respectively. The IOS indicator 114 generally provides a perceptible cue that suggests whether or not a particular defibrillation event will likely terminate the arrhythmic episode of the victim 102. For example, when the IOS indicator 114 displays a success indication of "88%," a rescuer (not shown) can be instructed "Press to Shock" to apply a shock to the victim 102 via actuation of a control 116. Other embodiments are possible. For example, it will be appreciated that a success indication may be implemented as any type of perceptible feedback (e.g., haptic, audio, etc.) as desired. In certain implementations, the defibrillator 104 may make the determination of a likelihood of success without expressly notifying the rescuer, and may simply use the determination to determine when to tell the rescuer that a shock may be delivered. In other situations, the defibrillator 104 may explicitly indicate the likelihood of success, such as by showing a percentage likelihood as indicated in FIG. 1, by showing less discrete gradations for success (e.g., poor, good, very good, and excellent), or by displaying a range of colors (e.g., with red indicating a poor chance and green indicating a good chance).

Figure 2:
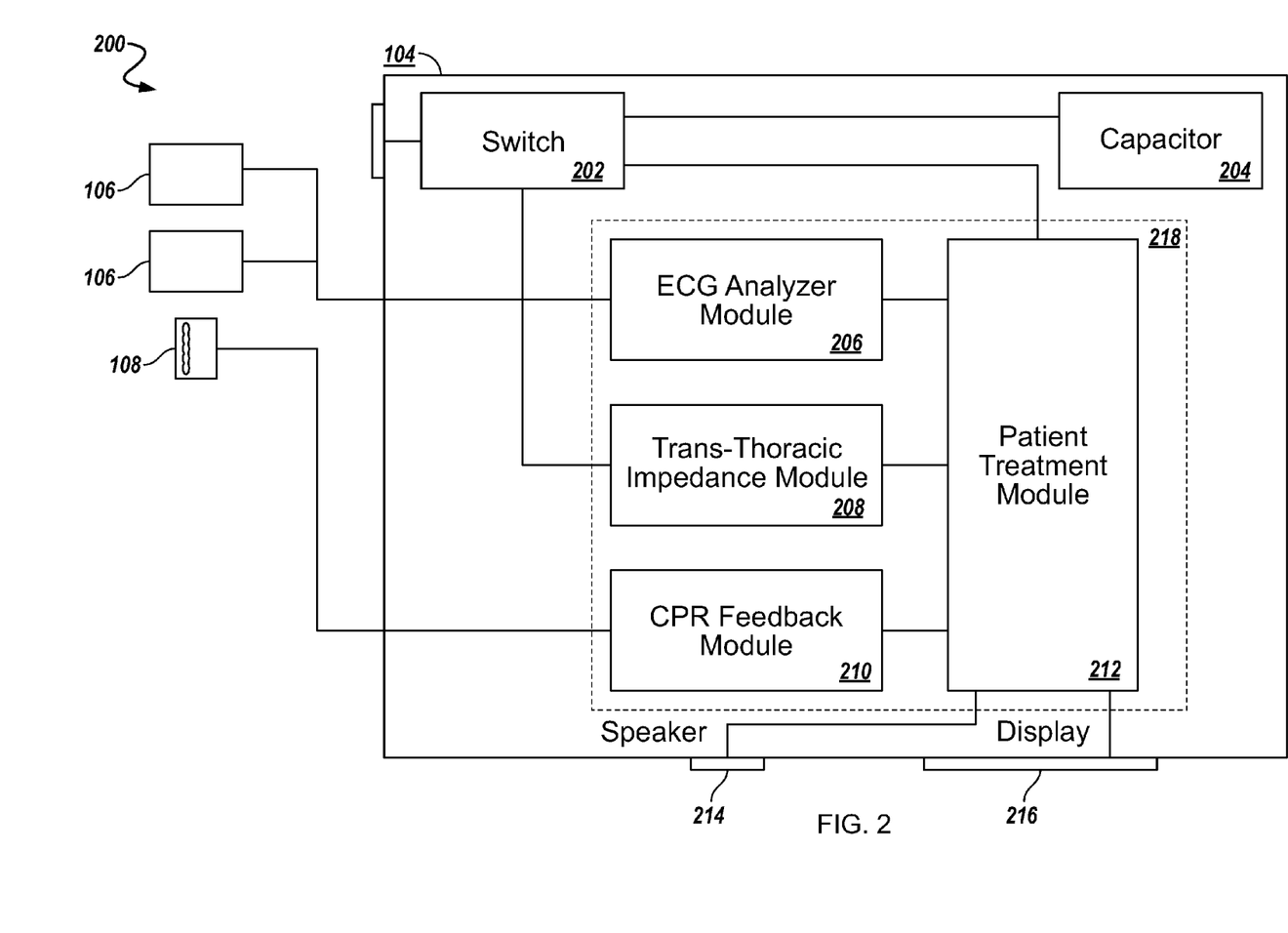
FIG. 2 is a schematic block diagram that shows a defibrillator with an electrode package and compression puck.

Referring now to FIG. 2, a schematic block diagram 200 shows the example defibrillator 104, along with the example electrode package 106 and compression puck 108, of FIG. 1 in more detail. In general, the defibrillator 104, and optionally one or more of the electrode package 106 and compression puck 108, defines an apparatus for administering care to a patient, subject, or individual (e.g., victim 102) who requires cardiac assistance.

The defibrillator 104 includes a switch 202 and at least one capacitor 204 for selectively supplying or applying a shock to a subject. The defibrillator 104 further includes an ECG analyzer module 206, a TTI module 208, a CPR feedback module 210 that controls frequency and magnitude of chest compressions applied to a subject, a patient treatment (PT) module 212, a speaker 214, and a display 216. In this example, the ECG analyzer module 206, TTI module 208, CPR feedback module 210, and patient treatment (PT) module 212 are grouped together as a logical module 218, which may be implemented by one or more computer processors. For example, respective elements of the logical module 218 can be implemented as: (i) a sequence of computer implemented instructions executing on at least one computer processor of the defibrillator 104; and (ii) interconnected logic or hardware modules within the defibrillator 104, as described in further detail below in connection with FIG. 6.

In the example of FIG. 2, the electrode package 106 is connected to the switch 202 via port on the defibrillator 103 so that different packages may be connected at different times. The electrode package may also be connected through the port to ECG analyzer module 206, and TTI module 208.

The compression puck 108 is connected, in this example, to the CPR feedback module 210. In one embodiment, the ECG analyzer module 206 is a component that receives an ECG (e.g., ECG signal 112). Similarly, the TTI module 208 is a component that receives transthoracic impedance (e.g., TTI signal 110). Other embodiments are possible The PT module 212 is configured to receive an input from each one of the ECG analyzer module 206, TTI module 208, and CPR feedback module 210. The PT module 212 uses inputs as received from at least the ECG analyzer module 206 and TTI module 208 to predict whether a defibrillation event will likely terminate an arrhythmic episode. In this manner, the PT module 212 uses information derived from both an ECG signal and transthoracic impedance measurement to provide a determination of a likelihood of success for delivering a defibrillating shock to a subject.

The PT module 216 is further configured to provide an input to each one of the speaker 214, display 216, and switch 202. In general, input provided to the speaker 214 and a display 216 corresponds to either a success indication or a failure indication regarding the likelihood of success for delivering a shock to the subject. In one embodiment, the difference between a success indication and a failure indication is binary and based on a threshold. For example, a success indication may be relayed to the display 216 when the chances corresponding to a successful defibrillation event is greater than 75%. In this example, the value "75%" may be rendered on the display 216 indicating a positive likelihood of success. When a positive likelihood of success is indicated, the PT module 216 enables the switch 202 such that a shock may be delivered to a subject.

In another embodiment, likelihood of a successful defibrillation event may be classified into one of many possible groups such as, for example, low, medium, and high likelihood of success. With a "low" likelihood of success (e.g., corresponding to a successful defibrillation event is less than 50%), the PT module 216 disables the switch 202 such that a shock cannot be delivered to a subject. With a "medium" likelihood of success (e.g., corresponding to a successful defibrillation event is greater than 50% but less than 75%), the PT module 216 enables the switch 202 such that a shock may be delivered to a subject, but also renders a warning on the display 216 that the likelihood of success is questionable. With a "high" likelihood of success (e.g., corresponding to a successful defibrillation event is greater than or equal to 75%), the PT module 216 enables the switch 202 such that a shock may be delivered to a subject, and also renders a cue on the display 216 indicating that the likelihood of success is very good. Still other embodiments are possible.

Figure 3:
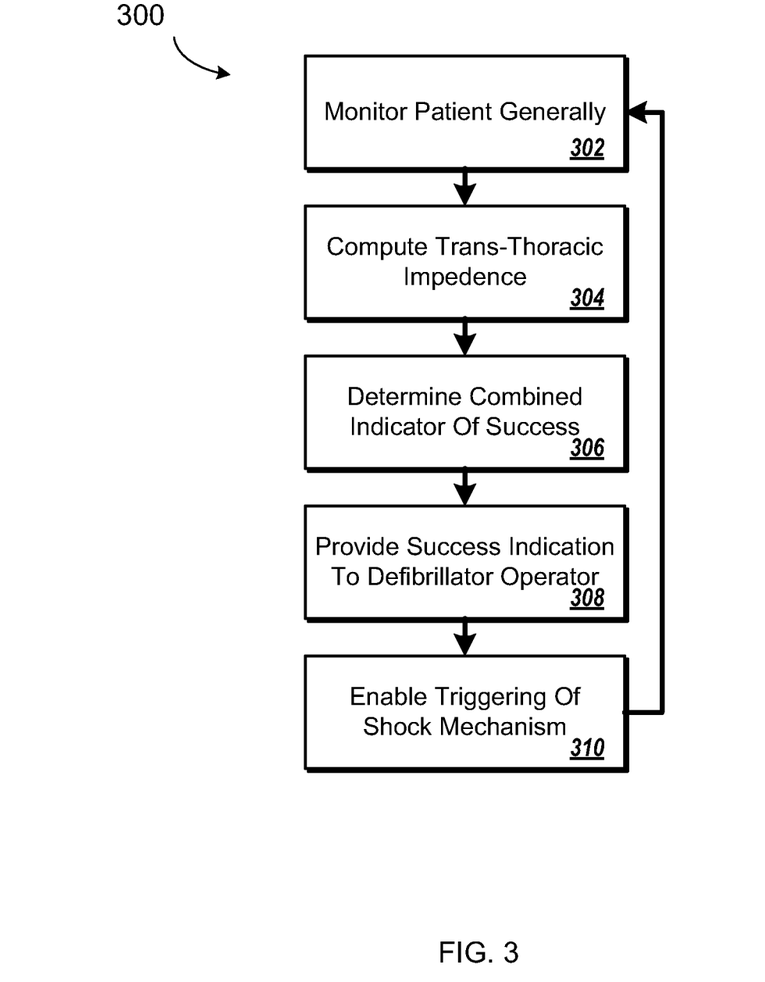
FIG. 3 is a flow chart of a process for providing a user with feedback regarding a likelihood that a defibrillating shock will be successful.

Referring now to FIG. 3, an example method 300 is shown for administering care to an individual requiring cardiac assistance. In one embodiment, the method 300 is implemented by the example defibrillator 104 described above in connection with FIGS. 1 and 2. However, other embodiments are possible.

At a step 302, at least one of an ECG signal (e.g., ECG signal 112) and a TTI signal (e.g., TTI signal 110) of the subject receiving cardiac care is monitored. In general, an individual receiving cardiac care includes the individual at any time during a cardiac event, including whether or not individual is receiving active care (e.g., chest compressions).

At a step 304, a TTI value is extracted from the TTI signal as monitored at step 302. In general, TTI values are inversely proportional to thoracic fluid content. For example, a TTI value of about 100 ohms approximately indicates presence of substantial thoracic fluid content (e.g., a "wet" patient), and a TTI value of about 180 ohms approximately indicates absence of thoracic fluid content (e.g., a "dry" patient).

Additionally, at step 304, an AMSA value is calculated from the ECG signal as monitored at step 302 by integrating the Fourier transform (e.g., FFT) of the ECG signal over a finite frequency range. Example frequency content of an arrhythmic ECG signal generally ranges between about 1 Hz to about 40 Hz, with amplitude of about 50 mV or less. An example of an AMSA value calculated from such a signal ranges between about 5 mV-Hz to about 20 mV-Hz. It will be appreciated however that this is only an example, and that the magnitude and spectra of an ECG signal ranges greatly.

At a step 306, the process determines a combined indicator of success that includes a indication from transthoracic impedance and an indication from an ECG reading, such as an AMSA indication. The combined indicator may be determined by inputting a TTI value and an AMSA value into a function or look-up table, or may be determined without a need to compute both values first, such as by taking inputs indicative of both values and computing a predictor of success directly from such indicative values.

At box 308, a success indication is provided to a defibrillator operator. The indication may take a variety of forms. For example, the ability of the defibrillator to deliver a shock may be enable when the indicator of success is higher than a threshold level. Also, the user may be notified that the defibrillator can provide a shock, and may be prompted to push a physical button to cause the shock to be delivered.

The user may also be provided with more detail about the success indication. For example, the user may be shown a percentage number that indicates a likelihood in percent that the shock will be successful. Alternatively, or in addition, the user may be show a less granular level of an indication, such as a value of "excellent," "good," and "poor" to indicate to the user what the likelihood of successful defibrillation is.

At box 310, the trigger mechanism is enabled on the defibrillator, as discussed above. In certain instances, such a feature may be enabled whenever a shockable rhythm is observed for a patient. In other circumstances, the enabling may occur only when the combined indication discussed above exceeds a threshold value for indicating that a shock will be successful in defibrillating the patient.

Figure 4A:
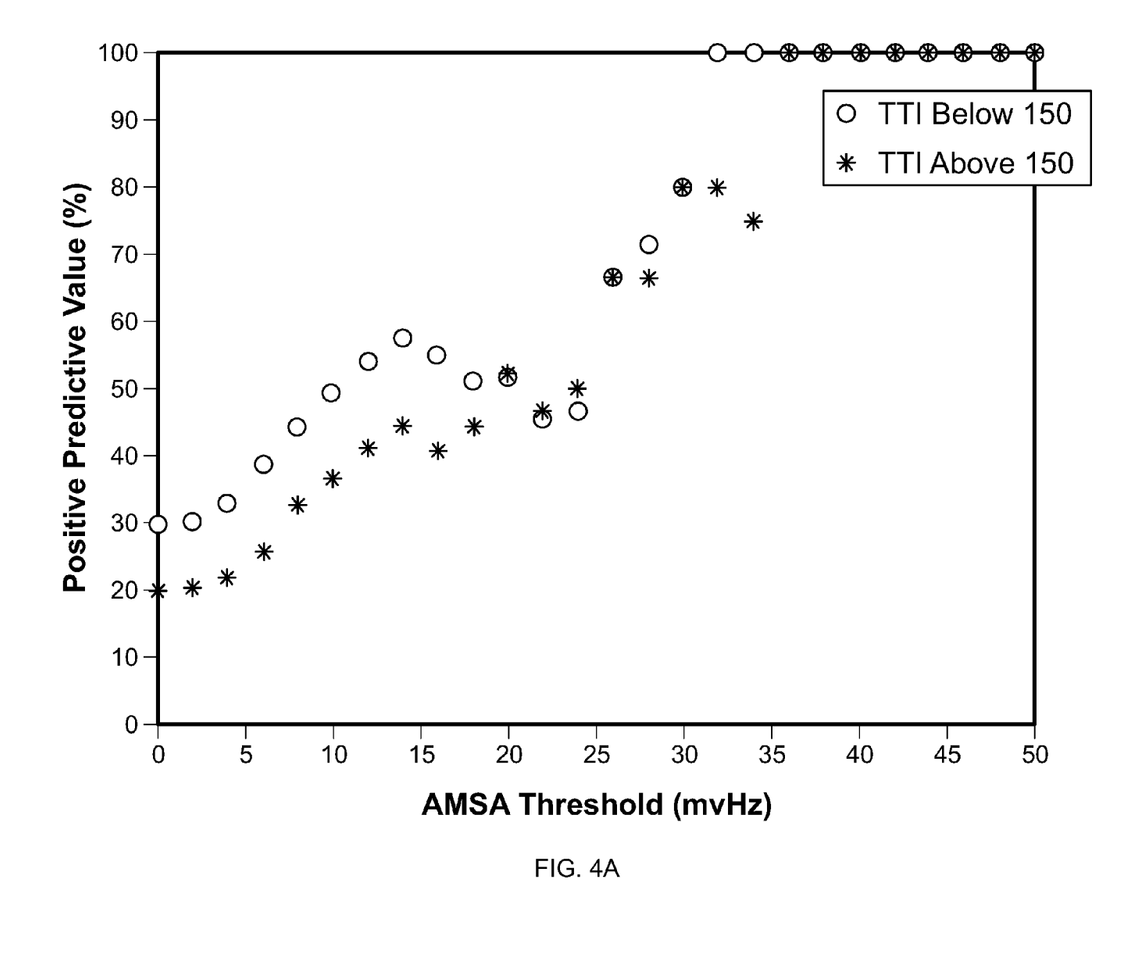
FIGS. 4A and 4B are graphs showing relationships between patient outcome and AMSA threshold values for groups of patients having different trans-thoracic impedance values.

FIG. 4A shows a plot of positive predictive value (%) versus AMSA threshold (mv-Hz) for a first set of subjects having a TTI measured greater than 150 ohms and a second set of subjects having a TTI measured less than 150 ohms. As shown by the comparative data, the first set of subjects generally has a greater positive predictive value for a given AMSA threshold. In both cases, positive predictive value generally increases with increasing AMSA threshold. Thus, an indication of success for a patient having a low impedance may be provided when the AMSA value is lower, than for a comparable AMSA value from a high impedance patient. Or, where a percentage likelihood of success is shown, the displayed percentage for a particular AMSA value may be higher for a low impedance patient as compared to a high impedance patient—at least with the range of AMSA values from 5-20 mv-HZ.

Figure 4B:
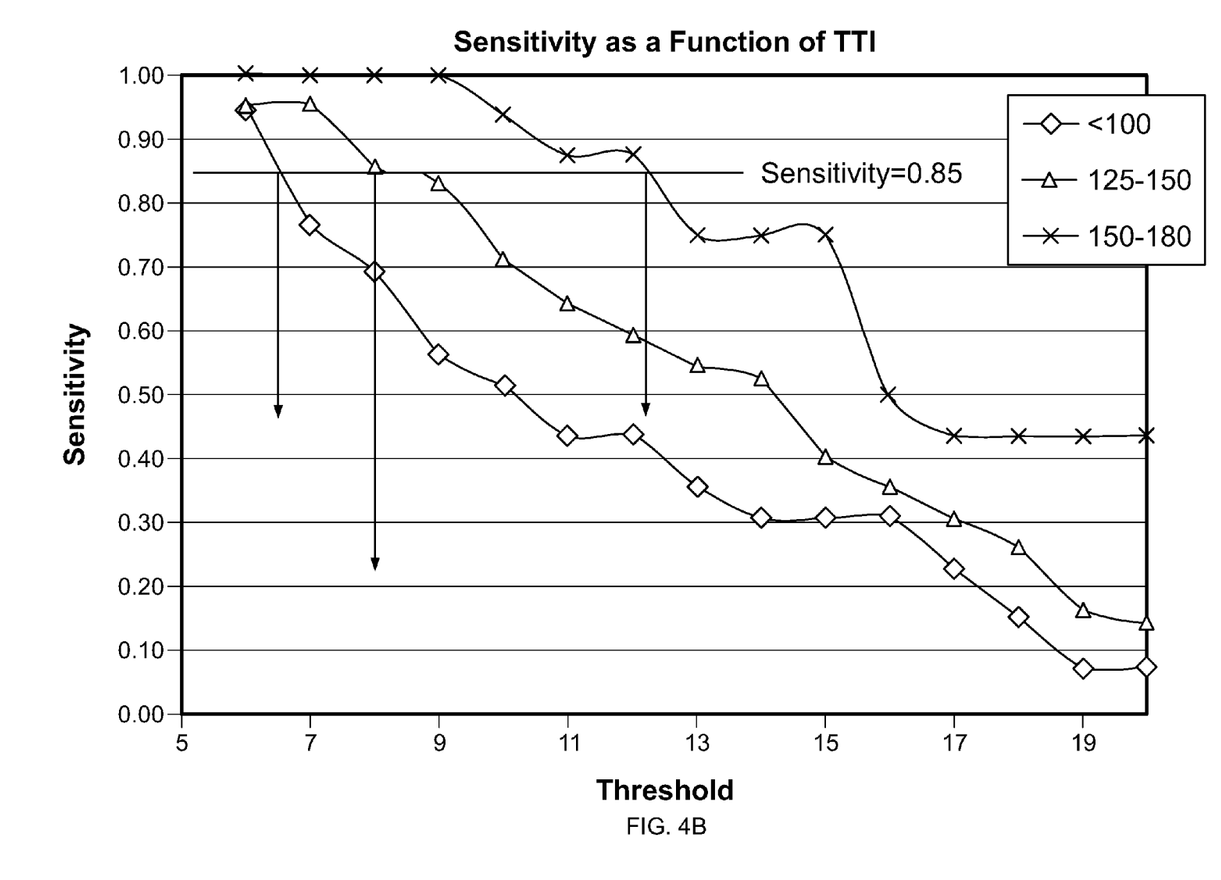

FIG. 4B shows a plot of sensitivity (unitless) versus AMSA threshold (mv-Hz) for a first set of subjects having a TTI measured less than 100 ohms, a second set of subjects having a TTI measured between 125 ohms and 150 ohms, and a third set of subjects having a TTI measured between 150 ohms and 180 ohms. As shown by the comparative data, AMSA threshold generally increases, for a given specificity, with increasing TTI.

Figure 5A:
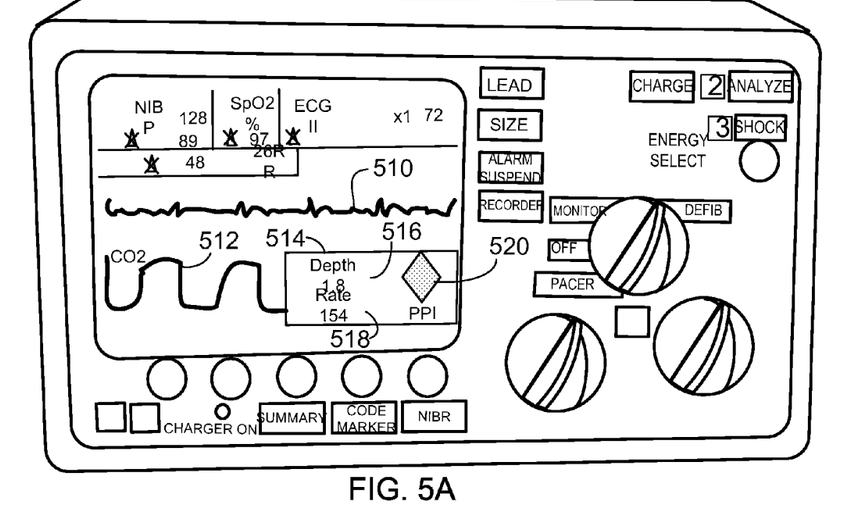
FIGS. 5A and 5B illustrate a defibrillator showing certain types of information that can be displayed to a rescuer.

FIG. 5A shows a defibrillator showing certain types of information that can be displayed to a rescuer. In the figure, a defibrillation device 500 with a display portion 502 provides information about patient status and CPR administration quality during the use of the defibrillator device. As shown on display 502, during the administration of chest compressions, the device 500 displays information about the chest compressions in box 514 on the same display as is displayed a filtered ECG waveform 510 and a $CO_2$ waveform 512 (alternatively, an $SpO_2$ waveform can be displayed).

During chest compressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions During Chest Compressions, the contents of which are hereby incorporated by reference in their entirety.

Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

The CPR information in box 514 is automatically displayed when compressions are detected by a defibrillator. The information about the chest compressions that is displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 514 also includes a perfusion performance indicator (PPI) 520. The PPI 520 is a shape (e.g., a diamond) with the amount of fill that is in the shape differing over time to provide feedback about both the rate and depth of the compressions. When CPR is being performed adequately, for example, at a rate of about 100 compressions per minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

As shown in display 500, the filtered ECG waveform 510 is a full-length waveform that fills the entire span of the display device, while the second waveform (e.g., the $CO_2$ waveform 512) is a partial-length waveform and fills only a portion of the display. A portion of the display beside the second waveform provides the CPR information in box 514. For example, the display splits the horizontal area for the second waveform in half, displaying waveform 512 on left, and CPR information on the right in box 514.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 521 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 521 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Figure 5B:
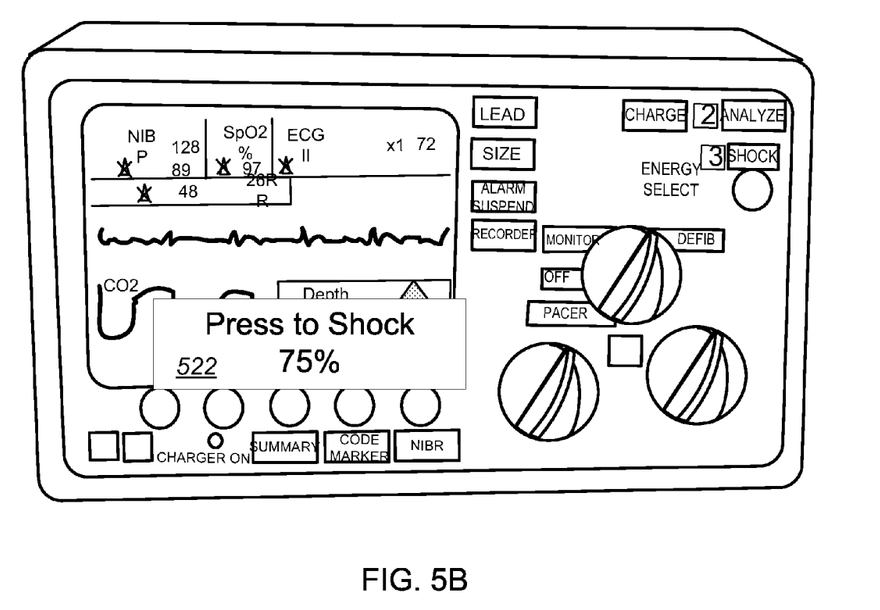

FIG. 5B shows the same defibrillator, but with an indicator box 522 now shown across the bottom half of the display and over the top of information that was previously displayed to display a success indication of "75%." Similar to the display 216 as described above, the indicator box 522 can generally convey a success indication or a failure indication regarding the likelihood of success for delivering a shock to a subject. In the example shown, the success indication is textual; however the success indication (and/or failure indication) can generally be implemented as any type of perceptible feedback. For example, tone, color, and/or other perceptible visual effects can be rendered or otherwise displayed to a user via the indicator box. For example, the characters "75%" may be highlighted or otherwise distinguished in a bold color, and the phrase "Press to Shock" may blink at least intermittently to convey a sense of urgency with respect to a pending shock. Other embodiments are possible.

Figure 6A:
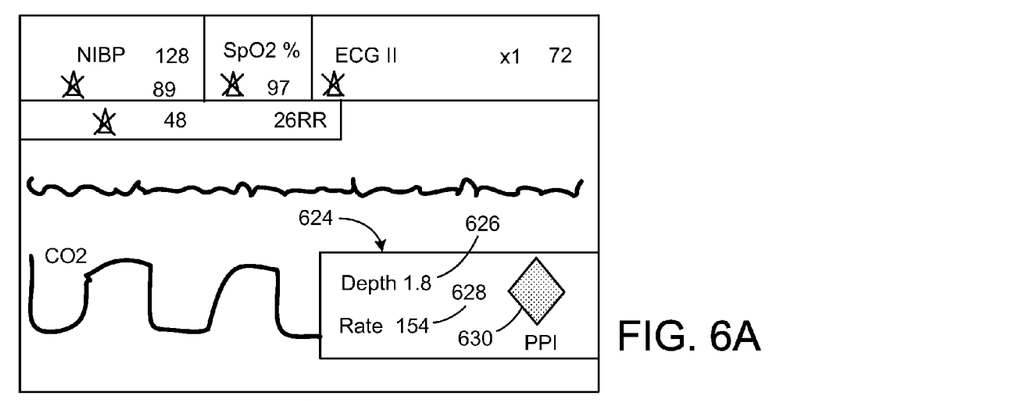
FIGS. 6A-6C show screenshots of a defibrillator display that provides feedback concerning chest compressions performed on a victim.
Figure 6B:
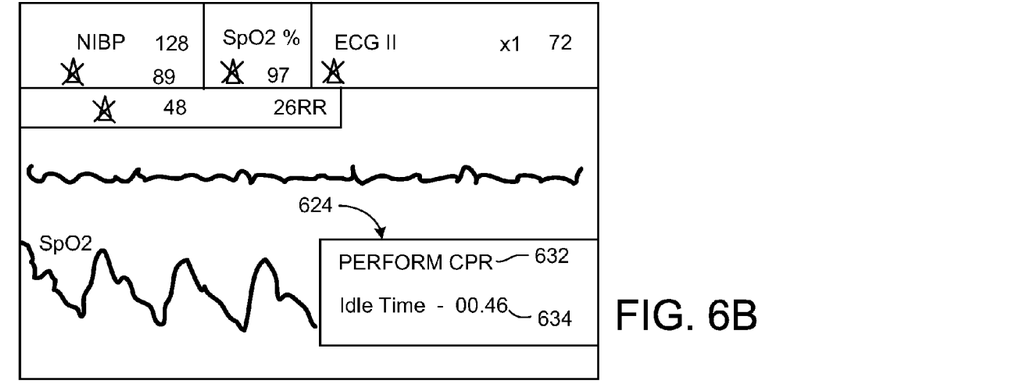
Figure 6C:
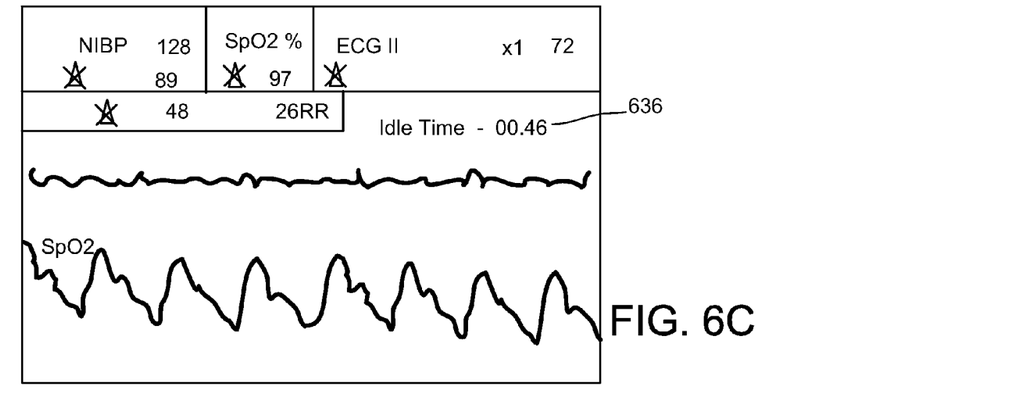

FIGS. 6A-6C show example screens that may be displayed to a rescuer on a defibrillator. Each of the displays may be supplemented with an indicator-like box 522 in FIG. 5B when the defibrillator makes a determination as to the likelihood of success for delivering a shock to a subject.

FIG. 6A shows exemplary information displayed during the administration of CPR chest compressions, while FIGS. 6B and 6C show exemplary information displayed when CPR chest compressions are not being sensed by the defibrillator. The defibrillator automatically switches the information presented based on whether chest compressions are detected. An exemplary modification of the information presented on the display can include automatically switching one or more waveforms that the defibrillator displays. In one example, the type of measurement displayed can be modified based on the presence or absence of chest compressions. For example, $CO_2$ or depth of chest compressions may be displayed (e.g., a $CO_2$ waveform 620 is displayed in FIG. 6A) during CPR administration, and upon detection of the cessation of chest compressions, the waveform can be switched to display an $SpO_2$ or pulse waveform (e.g., an $SpO_2$ waveform 622 is displayed in FIG. 6B).

Another exemplary modification of the information presented on the display can include automatically adding/removing the CPR information from the display upon detection of the presence or absence of chest compressions. As shown in FIG. 6A, when chest compressions are detected, a portion 624 of the display includes information about the CPR such as depth 626, rate 628, and PPI 630. As shown in FIG. 6B, when CPR is halted and the system detects the absence of CPR chest compressions, the defibrillator changes the CPR information in the portion 624 of the display, to include an indication 632 that the rescuer should resume CPR, and an indication 634 of the idle time since chest compressions were last detected. In a similar manner, when the defibrillator determines that rescuers should change, the label 632 can change to a message such as "Change Who is Administering CPR." In other examples, as shown in FIG. 6C, when CPR is halted, the defibrillation device can remove the portion of the display 624 previously showing CPR data and can display a full view of the second waveform. Additionally, information about the idle time 636 can be presented on another portion of the display.

Figure 7A:
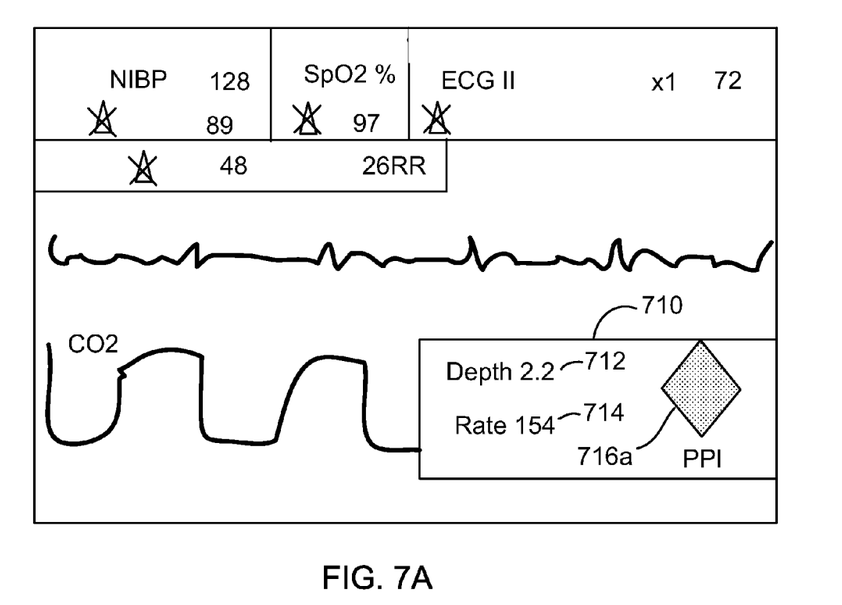
FIGS. 7A and 7B show screenshots providing feedback regarding a perfusion index created form chest compressions.
Figure 7B:
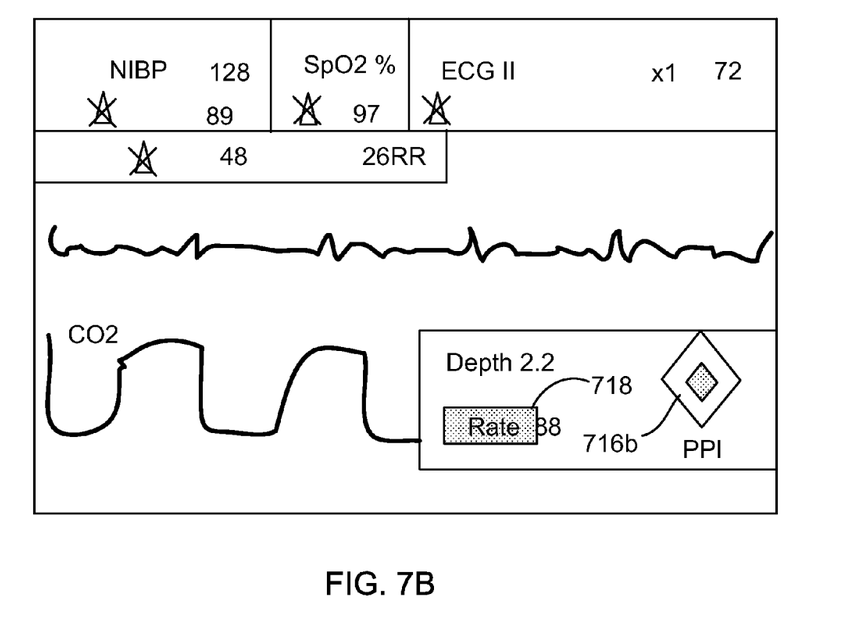

FIGS. 7A and 7B show defibrillator displays that indicate to a rescuer levels of perfusion being obtained by chest compressions that the rescuer is performing. FIG. 7A shows exemplary data displayed during the administration of CPR chest compressions when the CPR quality is within acceptable ranges, while FIG. 7B shows modifications to the display when the CPR quality is outside of the acceptable range.

In the example shown in FIG. 7B, the rate of chest compressions has dropped from 154 compressions per minute (FIG. 7A) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 718 to emphasize the rate information. In this example, the visual indication 718 is a highlighting of the rate information. Similar visual indications can be provided based on depth measurements when the depth of the compressions is shallower or deeper than an acceptable range of depths. Also, when the change in rate or depth indicates that a rescuer is becoming fatigued, the system may display a message to switch who is performing the chest compressions, and may also emit aural or haptic feedback to the same effect.

In the examples shown in FIGS. 7A and 7B, a perfusion performance indicator (PPI) 716 provides additional information about the quality of chest compressions during CPR. The PPI 716 includes a shape (e.g., a diamond) with the amount of fill in the shape differing based on the measured rate and depth of the compressions. In FIG. 7A, the depth and rate fall within the acceptable ranges (e.g., at least 100 compressions/minute (CPM) and the depth of each compression is greater than 1.5 inches) so the PPI indicator 716a shows a fully filled shape. In contrast, in FIG. 7B, when the rate has fallen below the acceptable range, the amount of fill in the indicator 716b is lessened such that only a portion of the indicator is filled. The partially filled PPI 716b provides a visual indication of the quality of the CPR is below an acceptable range.

As noted above with respect to FIG. 5A, in addition to measuring information about the rate and depth of CPR chest compressions, in some examples the defibrillator provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial. In addition, such factors may be included in a determination of whether the rescuer's performance has deteriorated to a level that the rescuer should be instructed to permit someone else perform the chest compressions, and such information may be conveyed in the various manners discussed above.

Figure 8A:
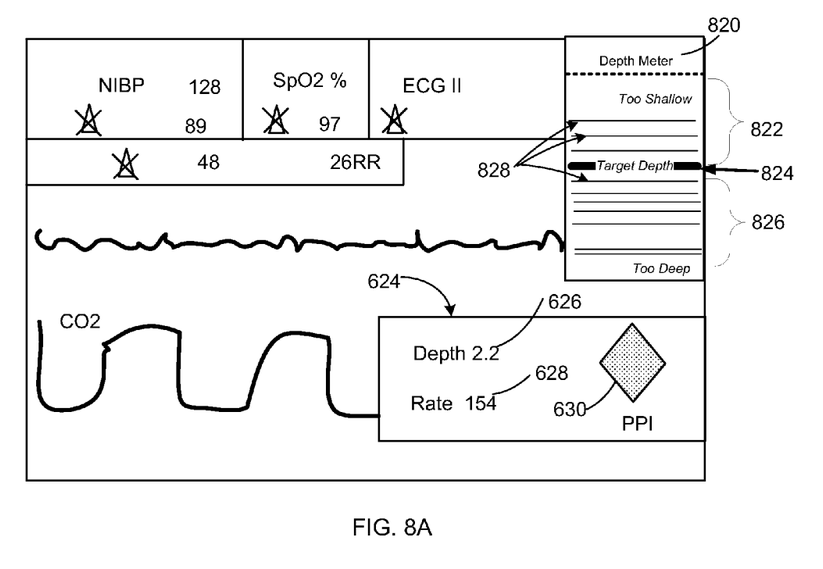
FIGS. 8A and 8B show screenshots with gradiated scales indicating target chest compression depths.

As shown in FIG. 8A, a visual representation of CPR quality can include an indicator of CPR compression depth such as a CPR depth meter 820. The CPR depth meter 820 can be automatically displayed upon detection of CPR chest compressions.

On the CPR depth meter 820, depth bars 828 visually indicate the depth of the administered CPR compressions relative to a target depth 824. As such, the relative location of the depth bars 828 in relation to the target depth 824 can serve as a guide to a rescuer for controlling the depth of CPR compressions. For example, depth bars 828 located in a region 822 above the target depth bar 824 indicate that the compressions were shallower than the target depth, and depth bars 828 located in a region 826 below the target depth bar 824 indicate that the compressions were deeper than the target depth. Again, then depth is inadequate (along with perhaps other factors) for a sufficient time to indicate that the rescuer is fatiguing, an indicator to switch rescuers may be provided in the manners discussed above.

Figure 8B:
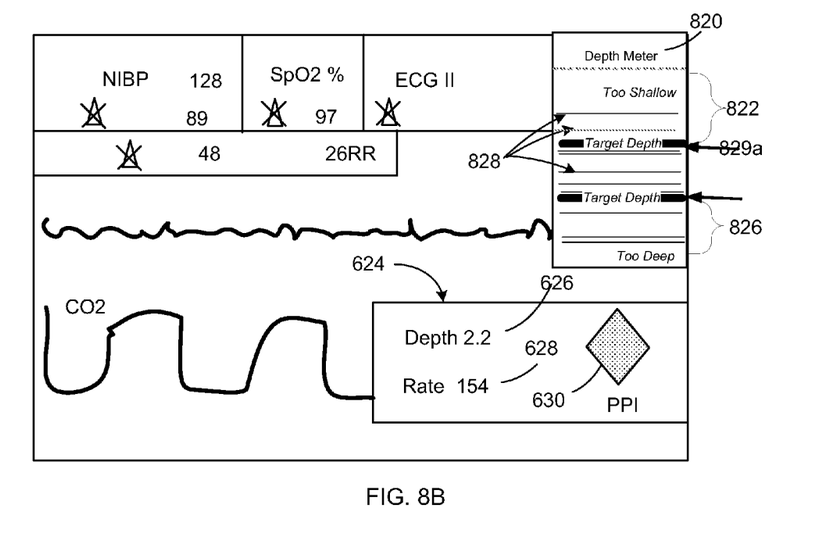

While the example shown in FIG. 8A displayed the target depth 824 as a single bar, in some additional examples, the target depth can be displayed as a range of preferred depths. For example, two bars 829a and 829b can be included on the depth meter 820 providing an acceptable range of compression depths (e.g., as shown in FIG. 8B). Additionally, in some examples, compressions that have depths outside of an acceptable range can be highlighted in a different color than compressions that have depths within the acceptable range of compression depths.

The depth bars 828 displayed on the CPR depth meter 820 can represent the compression depths of the most recent CPR compressions administered by the rescuer. For example, the CPR depth meter 820 can display depth bars 828 for the most recent 10-20 CPR compressions (e.g., the most recent 10 CPR compressions, the most recent 15 compressions, the most recent 20 CPR compressions). In another example, CPR depth meter 820 can display depth bars 828 for CPR compressions administered during a particular time interval (e.g., the previous 10 seconds, the previous 20 seconds).

In some additional embodiments, physiological information (e.g., physiological information such as end-tidal CO2 information, arterial pressure information, volumetric CO2, pulse oximetry (presence of amplitude of waveform possibly), and carotid blood flow (measured by Doppler) can be used to provide feedback on the effectiveness of the CPR delivered at a particular target depth. Based on the physiological information, the system can automatically determine a target CPR compression depth (e.g., calculate or look-up a new CPR compression target depth) and provide feedback to a rescuer to increase or decrease the depth of the CPR compressions. Thus, the system can provide both feedback related to how consistently a rescuer is administering CPR compressions at a target depth, and feedback related to whether the target depth should be adjusted based on measured physiological parameters. If the rescuers does not respond to such feedback and continues performed sub-optimal CPR, the system may then display an additional message to switch out the person performing CPR chest compressions.

In some examples, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, may determine whether to make further adjustments to the target compression depth.

And again, the actual performance of the rescuer against the revised target may be continually monitored to determine when the rescuer's performance has fallen below an acceptable level, so that the rescuer and perhaps others may be notified to change who is performing the chest compressions. Also, each of the relevant parameters of patient condition discussed above with respect to the various screenshots may be made one of multiple inputs to a process for determining when rescuers who are performing one component of a rescue technique should be switched out with another rescuer, such as for reasons of apparent fatigue on the part of the first rescuer.

While at least some of the embodiments described above describe techniques and displays used during manual human-delivered chest compressions, similar techniques and displays can be used with automated chest compression devices such as the AUTOPULSE device manufactured by ZOLL Medical, MA.

Figure 9:
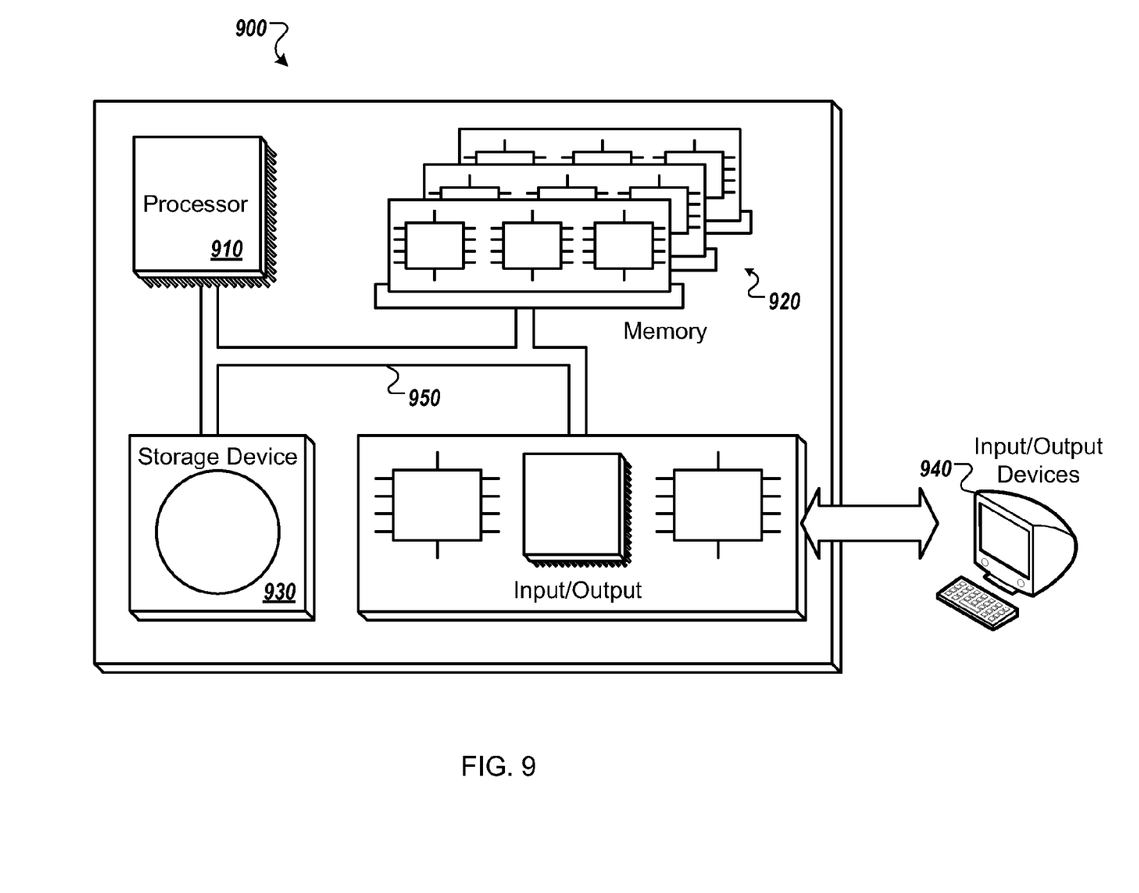
FIG. 9 shows a general computer system that can provide interactivity with a user of a medical device, such as feedback to a user in the performance of CPR.

The particular techniques described here may be assisted by the use of a computer-implemented medical device, such as a defibrillator that includes computing capability. Such defibrillator or other device is shown in FIG. 9, and may communicate with and/or incorporate a computer system 800 in performing the operations discussed above, including operations for computing the quality of one or more components of CPR provided to a victim and generating feedback to rescuers, including feedback to change rescuers who are performing certain components of the CPR. The system 900 may be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor may be designed using any of a number of architectures. For example, the processor 910 may be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 900. In one implementation, the storage device 930 is a computer-readable medium. In various different implementations, the storage device 930 may be a floppy disk device, a hard disk device, an optical disk device, or a tape device.

The input/output device 940 provides input/output operations for the system 900. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. One or more non-transitory machine-readable storage devices for managing care of a person receiving emergency cardiac assistance, the one or more machine-readable storage devices storing instructions that are executable by one or more processing devices to perform operations comprising:
    monitoring, with an external defibrillator, multiple parameters of the person receiving emergency cardiac assistance;
    determining from at least one of the multiple parameters, a value of trans-thoracic impedance of the person receiving emergency cardiac care;
    determining, from at least a second one of the multiple parameters corresponding to an electrocardiogram of the person receiving emergency cardiac assistance, one or more values representative of a likelihood of a shock effectiveness for the person receiving emergency cardiac assistance;

determining, as a function of at least the value of transthoracic impedance and the one or more values representative of the likelihood of the shock effectiveness, an indication of whether a shock provided to the person receiving emergency medical assistance will be effective in terminating an arrhythmic episode; and electrically energizing a switch of the external defibrillator or presenting an indicator of success to a rescuer as a result of determining the indication of whether the shock will be effective in terminating the arrhythmic episode.

2. The one or more non-transitory machine-readable storage devices of claim 1, further comprising instructions for repeating cyclically the operations of monitoring, determining, and affecting control over multiple time periods during provision of emergency cardiac assistance to the person.

3. The one or more non-transitory machine-readable storage devices of claim 1, further comprising instructions for identifying compression depth of chest compressions performed on the person, using a device on the person's sternum and in communication with the defibrillator, and providing feedback to the rescuer performing the chest compressions regarding rate of compression, depth of compression, or both.

4. The one or more non-transitory machine-readable storage devices of claim 1, wherein the multiple parameters comprise signals sensed by a plurality of electrocardiogram leads.

5. The one or more non-transitory machine-readable storage devices of claim 4, wherein determining an initial indicator of the likelihood of the shock effectiveness comprises determining a second value that is associated to an electrocardiogram amplitude at select frequencies or select frequency ranges.

6. The one or more non-transitory machine-readable storage devices of claim 5, wherein the determination of the initial indicator of the likelihood of the shock effectiveness comprises determining an amplitude spectrum area (AMSA) value.

7. The one or more non-transitory machine-readable storage devices of claim 1, wherein affecting control of the defibrillator comprises preventing a user from delivering the shock unless the determination of whether the shock will be effective in terminating the arrhythmic episode exceeds a determined likelihood level.

8. The one or more non-transitory machine-readable storage devices of claim 1, wherein affecting control of the defibrillator comprises electronically displaying an indicator of the indication of whether the shock will be effective.

9. The one or more non-transitory machine-readable storage devices of claim 8, wherein displaying an indicator comprises displaying each of the one or more values representative of the likelihood of the shock effectiveness in a range.

10. The one or more non-transitory machine-readable storage devices of claim 1, wherein determining an indication of whether a shock provided to the person receiving emergency medical assistance will be effective in terminating the arrhythmic episode comprises:
providing the value of the trans-thoracic impedance and the one or more values representative of the likelihood of the shock effectiveness as separate inputs to the function or a look-up table; and
determining the indication of whether the shock will be effective in terminating the arrhythmic episode in using an output of the function or a look-up table.

11. The one or more non-transitory machine-readable storage devices of claim 1, wherein the external defibrillator is a dual-mode defibrillator having a basic automatic mode and an advanced manual mode, and is programmed to affect control by the rescuer operating the switch or an electronic presentation device in a different manner depending on a current mode, in which the external defibrillator is set.

12. The one or more non-transitory machine-readable storage devices of claim 1, wherein a Fourier transform is applied to determine one or more AMSA values for the person receiving emergency cardiac assistance, the one or more AMSA values indicated in a form comprising V-Hz units.

13. The one or more non-transitory machine-readable storage devices of claim 12, wherein determining an initial indication of the likelihood of the shock effectiveness comprises comparing the one or more AMSA values to one or more predetermined AMSA thresholds.

14. The one or more non-transitory machine-readable storage devices of claim 1, further comprising identifying a motion applied to the chest of the person receiving emergency medical assistance as a result of applied chest compressions, and filtering the multiple parameters based on the motion.

15. One or more non-transitory machine-readable storage devices storing instructions that are executable by one or more processing devices to perform operations comprising:
generating first information indicative of an electrocardiogram of a person;
generating second information comprising a value of a trans-thoracic impedance of the person;
determining a likelihood of success from delivering a defibrillating shock to the person based on a function of at least the first and second information; and
providing to a user of a defibrillator an indication of the determination of the likelihood of success.

16. The one or more non-transitory machine-readable storage devices of claim 15, wherein the determining comprises combining the information indicative of the electrocardiogram of the person and the information indicative of the trans-thoracic impedance of the person as separate inputs to a formula or a look-up table.

* * * * *